United States Patent
Lubrecht

(10) Patent No.: US 6,243,938 B1
(45) Date of Patent: Jun. 12, 2001

(54) LOW SILICONE PLASTIC PREFILLABLE SYRINGE

(75) Inventor: Thea E. Lubrecht, Randolph, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/265,676

(22) Filed: Mar. 10, 1999

Related U.S. Application Data

(60) Provisional application No. 60/078,264, filed on Mar. 17, 1998.

(51) Int. Cl.[7] ............... B23P 25/00; B23P 11/02; B29B 15/00; B32B 18/00
(52) U.S. Cl. ............... 29/458; 29/450; 264/233; 264/134
(58) Field of Search ............... 29/777, 778, 450, 29/458; 264/169, 213, 130, 338, 447, 494, 488, 134, 349, 233

(56) References Cited

U.S. PATENT DOCUMENTS

| | | | |
|---|---|---|---|
| 4,197,333 | * | 4/1980 | Leach et al. ............ 427/54.1 |
| 4,806,430 | | 2/1989 | Spielvogel et al. . |
| 4,872,572 | | 10/1989 | Schrooten . |
| 5,000,994 | | 3/1991 | Romberg et al. . |
| 5,061,252 | | 10/1991 | Dragosits . |
| 5,356,948 | * | 10/1994 | Payne, Jr. et al. ............ 522/75 |
| 5,445,771 | * | 8/1995 | Degan ............ 264/22 |
| 5,456,679 | * | 10/1995 | Balaban et al. ............ 604/892.1 |
| 5,456,940 | | 10/1995 | Funderbunk . |
| 5,533,993 | * | 7/1996 | Maier ............ 604/411 |
| 5,607,400 | * | 3/1997 | Thibault et al. ............ 604/230 |
| 5,667,840 | * | 9/1997 | Tingey et al. ............ 427/8 |
| 5,755,894 | * | 5/1998 | Bowman et al. ............ 134/22.12 |
| 5,807,605 | * | 9/1998 | Tingey et al. ............ 427/8 |
| 6,004,300 | * | 12/1999 | Butcher et al. ............ 604/222 |
| 6,042,765 | * | 3/2000 | Sugahara et al. ............ 264/46.1 |
| 6,046,141 | * | 4/2000 | Kurz et al. ............ 508/100 |

FOREIGN PATENT DOCUMENTS

| | | |
|---|---|---|
| 0092383A2 | 4/1983 | (EP) . |
| 0111724A2 | 11/1983 | (EP) . |
| 0570978A1 | 5/1993 | (EP) . |
| 0627474A1 | 4/1994 | (EP) . |
| 0651005A1 | 10/1994 | (EP) . |

* cited by examiner

Primary Examiner—Icuda Rosenbaum
Assistant Examiner—Marc Jimenez

(57) ABSTRACT

A method for lubricating a sealing member and a medicament chamber in a drug delivery device includes providing lubricating silicone on the surface of the stopper and within the plastic material of the chamber. The stopper preferably is first washed and rinsed in hot deionized water followed by drying. The dried sealing member is then tumbled with polymeric silicone and then irradiated at a target dose between 2.5 to 4.0 Mrads to cause the silicone molecules to bond with the elastomeric material of the stopper. The irradiated sealing members are then loaded in any of a series of chambers including syringes, pre-filled syringes, drug cartridges, and needleless injector ampules. The chamber preferably is made from a plastic material that has been mixed with a lubricating solution such as silicone when the plastic is compounded.

17 Claims, 2 Drawing Sheets

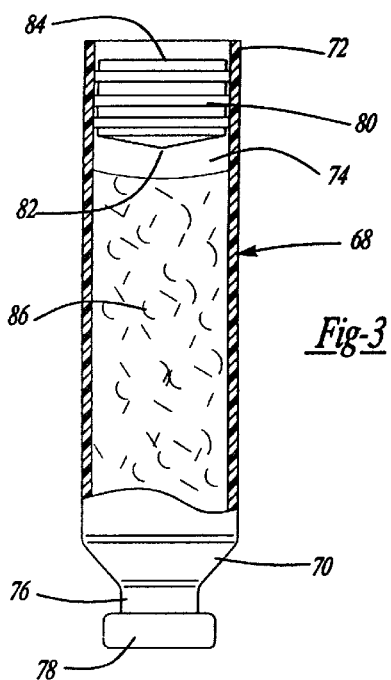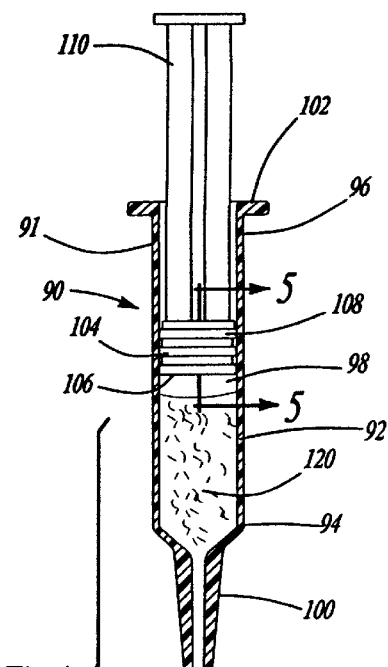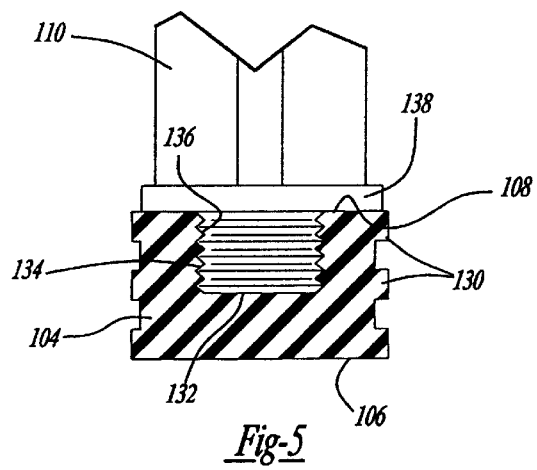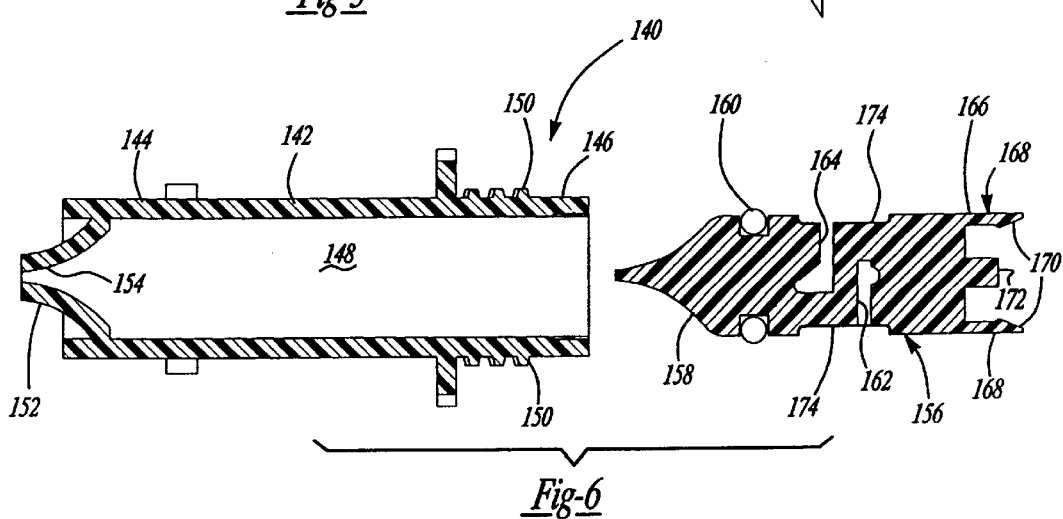

LOW SILICONE PLASTIC PREFILLABLE SYRINGE

This application claims the benefit of U.S. Provisional Application No. 60/078,264, filed Mar. 17, 1998.

BACKGROUND OF THE INVENTION

This invention generally relates to a method of lubricating the components of a drug delivery system and, more particularly, to a method of lubricating a sealing member and a drug holding chamber with a polymeric silicone.

Many drug delivery systems, like syringes, pre-filled syringes, drug cartridges and needleless injectors include an interior chamber for receiving a medicament and a sealing member. The sealing member is usually slidable within the interior chamber and in a fluid-tight relationship with the walls forming the interior chamber.

The sealing member can take many forms, with two conventional forms being a stopper and an O-ring. The sealing members are often made of rubber or elastomeric materials. The interior chamber of many drug delivery systems is made of plastic. The fluid-tight relationship between the sealing member and the wall forming the interior chamber provides a large resistance to movement of the sealing member within the interior chamber. Typically, this resistance has been reduced by pre-treating the walls of the interior chamber and the sealing member with a lubricating solution such as silicone. In the typical coating method, the sealing member is agitated with a solution of the silicone and then the sealing member is removed from the silicone solution and placed in the interior chamber of a drug delivery system. Typically, the surface of the walls of the interior chamber have also been pre-treated with a silicone solution.

There are several disadvantages with the typical lubricating method. The major disadvantage is that the lubricant typically is only loosely adhered to the sealing member or the interior chamber. This loose adherence permits the lubricating solution to become deposited into a medicament loaded in the drug delivery system. In some instances, spheres of silicone have been found suspended within the medicament solution.

Therefore, a drug delivery system that is lubricated in a manner that revents the lubricant from becoming deposited in the medicament is desirable. This invention includes lubricating the sealing member and the chamber material using techniques that prevent the lubricant from accumulating in the medicament.

SUMMARY OF THE INVENTION

In general terms, this invention is a medicament delivery device having two basic components. A chamber has a body made from a plastic material that includes a lubricating substance within the plastic. The chamber includes an inner surface for receiving the medicament. A sealing member is slidably received within the chamber and has an exterior surface that sealing engages the inner surface of the chamber. The sealing member outer surface includes a lubricating silicone substance on the outer surface. The lubricating silicone substance is adhered to the outer surface of the sealing member by cross linking bonds between molecules of the lubricating silicone. The cross linking bonds preferably are formed by irradiating the sealing member after the lubricating silicone has been applied to the outer surface.

In the most preferred embodiment, the lubricating silicone on the sealing member comprises a polydimethyl siloxane having a viscosity of approximately 100,000 centistokes.

The delivery device of this invention preferably is made by the method having the following basic steps. The chamber is formed by mixing a lubricating substance into a plastic material during the process of compounding the plastic material. The chamber is formed from the compounded plastic material that contains the lubricating substance within it. An outer surface of the sealing member is coated with a lubricating substance. The lubricating substance used within the plastic material for the chamber can be, but is not necessarily, the same lubricating substance used on the outer surface of the sealing member. Once the sealing member is coated, the sealing member and the lubricating substance are irradiated to induce cross linked bonds between the molecules of the lubricating substance so that the substance adheres to the outer surface of the sealing member. Then the sealing member is inserted into the chamber so that the outer surface of the sealing member sealingly engages the inner surface of the chamber.

These and other features and advantages of this invention will become more apparent to those skilled in the art from the following detailed description of the presently preferred embodiment. The drawings that accompany the detailed description can be described as follows.

BRIEF DESCRIPTION OF THE DRAWINGS

FIG. 3 is a side, cross-sectional view of a drug delivery cartridge.

FIG. 4 is an exploded, side view of a syringe and a needle cannula.

FIG. 5 is a cross-sectional, side view of a stopper and a plunger.

FIG. 6 is an exploded, side view of a medicament cartridge that can be used with a needleless injector.

DETAILED DESCRIPTION OF THE PREFERRED EMBODIMENT

Figure 1:
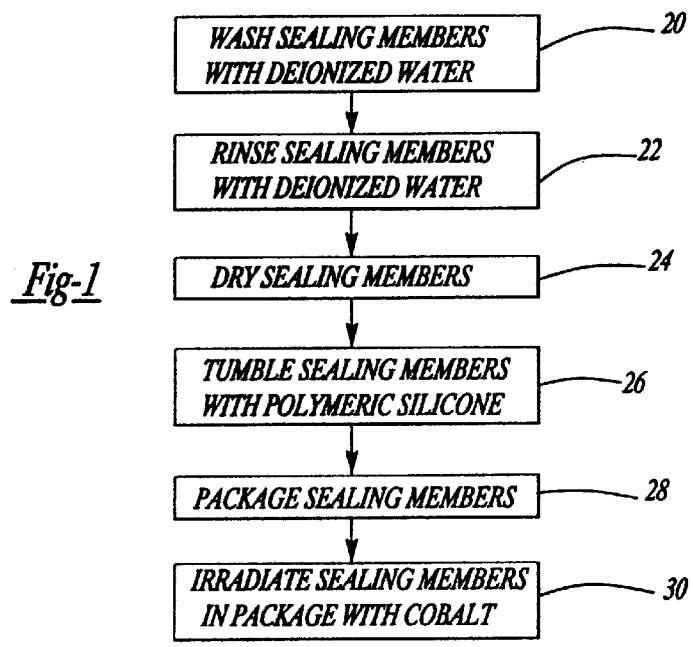
FIG. 1 is a flowchart illustrating the steps of lubricating a sealing member according to the method of this invention.

A flow chart of the method of this invention of lubricating a stopper member is provided in FIG. 1. In step 20, the sealing members are washed. Preferably the sealing members are washed with hot deionized water. Most preferably, the sealing members are washed in deionized water at a temperature between 154 and 181° F. for 1.5 minutes.

In step 22 the sealing members are rinsed. Preferably, the sealing members are rinsed in deionized water. Most preferably, the sealing members are rinsed in deionized water at a temperature between 154 and 181° F. for 7.5 minutes.

In step 24 the sealing members are dried. Most preferably, the sealing members are dried for 30 minutes at 200° F.

In step 26, the sealing members are tumbled with polymeric silicone to coat the sealing members. Most preferably, the sealing members are tumbled with polymeric silicone for 60 minutes to coat the sealing members. A conventional tumbling device can be used.

In step 28, the coated sealing members are packaged in a container. Most preferably, the coated sealing members are packaged and sealed in the container. In step 30, the packaged and coated sealing members are irradiated. Most preferably, the packaged and coated sealing members are irradiated with Cobalt radiation at a target dose of 2.5 to 4.0 Mrads. The radiation provides cross linking between the silicone molecules and adheres the silicone to the stopper. Thus, steps 20 through 30 produce a lubricated, sterile, sealing member.

This invention also includes forming a medicament receiving chamber from a plastic that has been mixed with a polymeric silicone to produce a pre-lubricated plastic material. The method preferably includes mixing a selected polymeric silicone with a plastic material during the compounding of the plastic material. Apart from the addition of the selected polymeric silicone, the compounding process is conventional. Preferably, the polymeric silicone used has a viscosity of approximately 100,000 centistokes. The plastic material containing a polymeric silicone can be formed into a variety of drug delivery devices as will be described more fully below. Prelubrication of the plastic material further reduces the resistance between the medicament chamber interior wall and a coated sealing member produced according to the method described above. Moreover, prelubrication of the plastic material during the plastic compounding procedure effectively eliminates the possibility for the lubricant to become deposited in the medicament. Further, since the plastic chamber is prelubricated, the assembly/manufacturing step of applying a lubricant to the inside of the chamber is eliminated.

Figure 2:
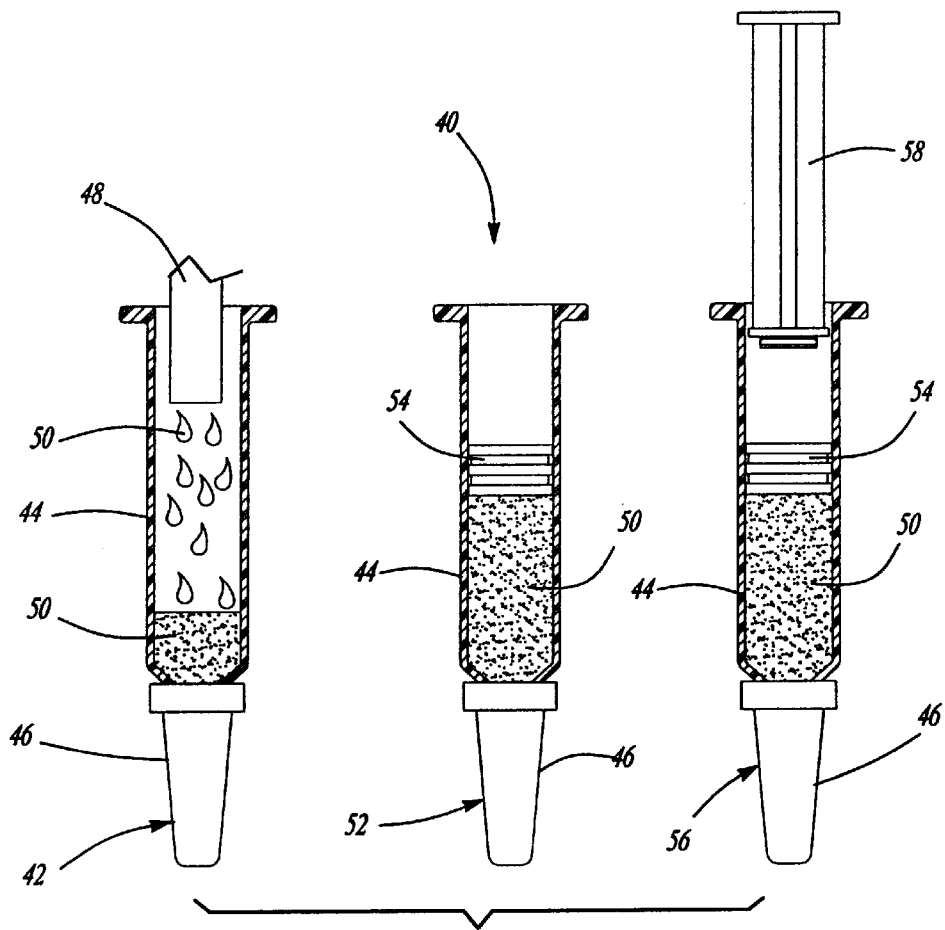
FIG. 2 is a schematic illustration of the processing steps of manufacturing a prefilled syringe assembly designed according to the present invention.

A schematic diagram of the processing steps of manufacturing a prefilled syringe using a lubricated sealing member designed according to the present invention is generally indicated at 40 in FIG. 2. As shown at 42, a plastic, pre-lubricated syringe 44 having a needle shield 46 receives a fill tube 48. The fill tube 48 dispenses a medicament 50 into the syringe 44 to fill the syringe 44. In the stage illustrated at 52, a coated, lubricated, and irradiated sealing member 54, preferably made according to the method described above, is inserted into the syringe 44 in a fluid-tight relationship over the medicament 50. At 56, a plunger 58 is inserted into the sealing member 54. Put another way, step 42 involves filling the syringe 44 with a medicament 50, step 52 involves placing a lubricated sealing member 54 into the syringe 44, and step 56 involves connecting the plunger 58 and the sealing member 54. Of course, the sealing member 54 and plunger 58 can be preassembled before step 52 is performed.

The particular polymeric silicone used to lubricate the sealing member 54 preferably is selected in order to be compatible with the particular medicament in the drug delivery system and the material composition of the sealing member. In addition, it is necessary to comply with federal regulations regarding acceptable materials for use in a drug delivery system.

Polymeric silicones that may be used with the method of this invention include: phenyl substitute silicones, vinyl substitute silicones, hydrogen substituted silicones, and others. One especially preferred silicone is known as Med-361, which is a polydimethyl siloxane, produced by Nusil and the most preferred viscosity of Med-361 is 100,000 centistokes. All of these silicones can be used at viscosities between 1,000 and 100,000 centistokes. Acceptable phenyl substituted silicones include: dimethyldiphenylpolysiloxane copolymers; dimethyl, methylphenylpolysiloxane copolymers; polymethylphenylsiloxane; and methylphenyl, dimethylsiloxane copolymers. The higher the phenyl content of the substituted silicone the lower the amount of radiation-induced crosslinking that occurs. The phenyl substituted silicones can be used in a variety of viscosities especially between 12,500 centistokes and 100,000 centistokes.

When compounding the silicone with a plastic, to form the chamber as described above, it is most preferred to use a silicone having a viscosity of 100,000 centistokes.

Vinyl substituted silicones that have been found to be advantageous in the method of this invention include: vinyldimethyl terminated polydimethylsiloxanes; vinylmethyl, dimethylpolysiloxane copolymers; vinyldimethyl terminated vinylmethyl, dimethylpolysiloxane copolymers; divinylmethyl terminated polydimethylsiloxanes; polydimethylsiloxane, mono vinyl, mono n-butyldimethyl terminated; and vinylphenylmethyl terminated polydimethylsiloxanes. The vinyl substituted silicones also can be made in a variety of viscosities as noted above. Higher vinyl content provides more efficient radiation induced crosslinking.

The hydrogen substituted silicones that have been found to be advantageous in the method of this invention include: dimethylhydro terminated polydimethylsiloxanes; methylhydro, dimethylpolysiloxane copolymers; methylhydro terminated methyloctyl siloxane copolymers; and methylhydro, phenylmethyl siloxane copolymers. The hydrogen substituted siloxanes can be used in a variety of viscosities as noted above.

Other substituted silicones that may be used in the method of this invention include: polyfluoroalkylmethyl siloxanes; fluoralkyl, dimethyl siloxane copolymers; and polymethylalkylsiloxanes.

FIGS. 3 through 6 illustrate example drug delivery assemblies that incorporate a lubricated sealing member and a prelubricated plastic medicament chamber made according to this invention. A plastic, pre-lubricated medicament cartridge is shown generally at 66 in FIG. 3. The medicament cartridge 66 comprises a generally cylindrical barrel 68 having a first end 70, a second end 72, and an interior chamber 74. A neck portion 76 is located adjacent the first end 70. A seal 78 surrounds an end of the neck portion 76 and seals the neck portion 76. A lubricated stopper 80, made according to the method described above, is received in a fluid-tight relationship into the interior chamber 74 through the second end 72 of the medicament cartridge 66. The stopper 80 includes a first side 82 and a second side 84. A medicament 86 is located between the first side 82 of the stopper 80 and the seal 78. As will be understood by those skilled in the art, such medicament cartridges 66 are designed to be received in a wide variety of delivery devices (not shown). The delivery devices include a needle cannula for penetrating the seal 78 and a plunger mechanism for moving the stopper 80 from the second end 72 toward the first end 70 to expel the medicament 86 from the interior chamber 74 during an injection.

An exploded side view of a plastic, pre-lubricated syringe and a needle cannula is generally indicated at 90 in FIG. 4. The syringe 91 includes a cylindrical barrel 92 made from a prelubricated plastic material containing one of the silicones listed above and having a first end 94 and a second end 96 and an interior chamber 98. A neck portion 100 is located adjacent the first end 94. A flange 102 is located adjacent the second end 96. A lubricated stopper 104, formed according to the method of this invention is received in a fluid-tight relationship into the interior chamber 98. The stopper 104 has a first side 106 and a second side 108. A plunger 110 is received in the second side 108 of the stopper 104. A needle cannula 112 includes a hub 114 and a needle 116. The neck portion 100 includes a fluid channel 118. A medicament 120 is located in the interior chamber 98 between the first side 106 of the stopper 104 and the neck portion 100. The needle cannula 112 is received on the neck portion 100. The fluid channel 118 is in fluid communication with the needle 116.

FIG. 5 is a cross-sectional side view of a portion of the plunger 110 and the lubricated stopper 104. The stopper 104 preferably includes a plurality of ribs 130. An interior space 132 extends from the second side 108 of the stopper 104 into the stopper 104. A set of internal threads 134 lines the interior space 132. A set of external threads 136 are located on the plunger 110 adjacent a plunger base 138. The internal threads 134 are adapted to receive the external threads 136.

An exploded side view of a pre-lubricated plastic cartridge for use with a needleless injector is shown at 140 in FIG. 6. The cartridge 140 includes a cylindrical barrel 142 having a first end 144, a second end 146, and an interior chamber 148. A luer lock arrangement 150 preferably is located adjacent the second end 146 for securing the cartridge 140 into a needleless injector. A tapered tip 152 is located adjacent the first end 144 and includes a fluid orifice 154.

A plunger 156 is slidably received in the interior chamber 148. The plunger 156 includes a tip portion 158 and a lubricated sealing member 160, formed according to the method of this invention, adjacent the tip portion 158. The sealing member 160 is in a fluid-tight relationship with the interior chamber 148 when the plunger 156 is received into the chamber 148. Preferably, the sealing member 160 is an O-ring. The plunger 156 further includes a first cutout 162 and a second cutout 164. A plunger portion 166 includes a series of spaced tabs 168 that facilitate cooperation between an injector driver member (not shown) and the plunger 156. A tab lip 170 is located on each of the spaced tabs 168. A boss 172 is located centrally to the spaced tabs 168. The plunger 156 further includes a pair of slots 174.

As will be understood by those skilled in the art, the needleless injector cartridge 140 is designed to be utilized with a variety of commercially available injector devices (not shown). The injector device driver mechanism is used to drive the plunger 156 from a position adjacent the second end 146 toward the first end 144 and expel a medicament (not shown) out of the interior chamber 148, through the fluid orifice 154 to accomplish a needleless injection.

As will be understood by those skilled in the art, all of the sealing members and stoppers are in fluid-tight relationship with the walls of the interior chambers. The sealing members and stoppers preferably are made of rubber or elastomeric materials. The specific embodiments described above are for illustration purposes only. A plurality of applications or uses for the lubrication methods of this invention have been shown.

The foregoing description is exemplary rather than limiting in nature. Variations and modifications to the disclosed embodiments may become apparent to those skilled in the art that still come within the scope of this invention. Accordingly, the scope of legal protection afforded this invention can only be determined by studying the following claims.

I claim:

1. A method of making a drug delivery assembly having a sealing member disposed within a medicament receiving chamber, comprising the steps of:
   (A) compounding a plastic material;
   (B) mixing a polymeric silicone into the plastic material while performing step (A);
   (C) forming the chamber from the compounded plastic material containing the polymeric silicone;
   (D) coating an outer surface on a sealing member with a polymeric silicone;
   (E) irradiating the coated sealing member with a radioisotope to thereby induce cross-linked bonds between molecules of the polymeric silicone and to adhere the polymeric silicone to the other surface; and
   (F) inserting the sealing member from step (D) into the chamber from step (C).

2. The method of claim 1, wherein step (B) includes using a polymeric silicone having a viscosity of approximately 100,000 centistokes.

3. The method of claim 1, wherein step (D) includes the substeps of
   washing the sealing member in deionized water;
   rinsing the sealing member in deionized water; and
   drying the sealing member prior to coating the outer surface.

4. The method of claim 3, wherein step (D) is performed by using deionized water having a temperature in the range from about 150 degrees F. to about 180 degrees F.

5. The method of claim 3, wherein step (D) is performed by drying the sealing member using a temperature of approximately 200 degrees F.

6. The method of claim 1, wherein step (D) is performed by tumbling the sealing member with the polymeric silicone.

7. The method of claim 1, wherein step (E) is performed by placing the sealing member in a sealed package and irradiating the sealing member and the sealed package using radio radioisotope radiation levels in the range from approximately 2.5 to about 4.0 Mrads.

8. The method of claim 1, wherein step (E) is performed using radioisotope Cobalt radiation.

9. The method of claim 1, wherein the polymeric silicone used in step (D) has a viscosity in the range from about 1,000 to about 100,000 centistokes.

10. The method of claim 9, wherein the viscosity of the polymeric silicone is greater than about 12,500 centistokes.

11. The method of claim 9, wherein said polymeric silicone comprises a polydimethyl siloxane.

12. The method of claim 1, wherein said polymeric silicone is one of the group of phenyl substituted silicones comprising dimethyldiphenylpolysiloxane copolymers; dimethyl, methylphenylpolysiloxaine copolymers; polymethylphenylsiloxane; and methylphenyl, dimethylsiloxane copolymers.

13. The method of claim 1, wherein step (F) is performed without placing any external lubricant on an interior surface of the chamber.

14. The method of claim 1, wherein said polymeric silicone is one of the group of vinyl substituted silicones comprising vinyldimethyl terminated polydimethylsiloxanes; vinylmethyl, dimethylpolysiloxane copolymers; vinyldimethyl terminated vinylmethyl, dimethylpolysiloxane copolymers; divinylmethyl terminated polydimethylsiloxanes; polydimethylsiloxane, mono, vinyl, mono n-butyldimethyl terminated; and vinylphenylmethyl terminated polydimethylsiloxanes.

15. The method of claim 1, wherein said polymeric silicone is one of the group of hydrogen substituted silicones comprising dimethylhydro terminated polydimethylsiloxanes; methylhydro, dimethylpolydimethylsiloxane copolymers; methylhydro terminated methyloctyl siloxane copolymers; and methylhydro, phenylmethyl siloxane copolymers.

16. The method of claim 1, wherein said polymeric silicone comprises polyfluoroalkylmethyl siloxanes; fluoroalkyl, dimethyl siloxane copolymers; and polymethylalkylsiloxanes.

17. The method of claim 1, comprising the further step of placing a medicament into the chamber formed in step (C) prior to inserting the sealing member from step (D) into the chamber from step (C) with the sealing member being in fluid contact with the medicament.

* * * * *